(12) United States Patent
O'Brien, III et al.

(10) Patent No.: US 7,796,729 B2
(45) Date of Patent: Sep. 14, 2010

(54) RADIOTHERAPY CHAMBER AND METHOD

(75) Inventors: William J. O'Brien, III, 231 S. Chancellor St., Newtown, PA (US) 18940; Joseph E. Underwood, Jr., Beverly, NJ (US)

(73) Assignee: William J. O'Brien, III, Newtown, PA (US)

( * ) Notice: Subject to any disclaimer, the term of this patent is extended or adjusted under 35 U.S.C. 154(b) by 221 days.

(21) Appl. No.: 12/029,931

(22) Filed: Feb. 12, 2008

(65) Prior Publication Data

US 2008/0192894 A1    Aug. 14, 2008

Related U.S. Application Data

(60) Provisional application No. 60/889,484, filed on Feb. 12, 2007.

(51) Int. Cl.
*A61G 10/00* (2006.01)
*H05G 1/04* (2006.01)

(52) U.S. Cl. ............... 378/65; 378/196; 128/205.26
(58) Field of Classification Search ............ 378/57, 378/62, 64, 65, 193, 195–197, 203, 204, 378/210; 128/202.12, 202.13, 202.16, 205.26
See application file for complete search history.

(56) References Cited

U.S. PATENT DOCUMENTS

| | | | |
|---|---|---|---|
| 3,209,990 A | 10/1965 | Akerman | |
| 3,588,499 A | 6/1971 | Pegrum | |
| 4,432,354 A | 2/1984 | Lasley | |
| 4,633,859 A * | 1/1987 | Reneau | 128/205.26 |
| 4,727,870 A * | 3/1988 | Krasle | 128/202.12 |
| 5,327,904 A * | 7/1994 | Hannum | 128/205.26 |
| 6,011,563 A * | 1/2000 | Fournier et al. | 606/2 |
| 6,016,803 A * | 1/2000 | Volberg et al. | 128/205.26 |
| 6,321,746 B1 * | 11/2001 | Schneider et al. | 128/202.12 |
| 6,749,405 B2 * | 6/2004 | Bassine | 417/313 |
| 6,827,760 B2 * | 12/2004 | Kutt et al. | 95/8 |
| 2008/0210234 A1 * | 9/2008 | O'Brien et al. | 128/202.12 |

OTHER PUBLICATIONS

International Preliminary Report on Patentability issued on PCT/US08/53719.

* cited by examiner

*Primary Examiner*—Edward J Glick
*Assistant Examiner*—Thomas R Artman

(57) ABSTRACT

A radiotherapy chamber is provided that comprises a substantially air-tight enclosure adapted to accept a patient; a radiation source disposed inside the enclosure; a patient support system disposed inside the enclosure and in working arrangement with the radiation source; and a screw compressor and an outlet flow modulator fluidly connected to the enclosure. A method for treatment of a subject in need thereof using the radiation chamber is also provided.

14 Claims, 5 Drawing Sheets

RADIOTHERAPY CHAMBER AND METHOD

This application claims the benefit of U.S. Provisional Application Ser. No. 60/889,484, filed on Feb. 12, 2007, incorporated herein by reference in its entirety.

FIELD OF THE INVENTION

The present invention relates to an apparatus and method for radiation therapy. More specifically, the invention relates to a hyperbaric chamber to be used in combination with radiotherapy.

BACKGROUND OF THE INVENTION

Radiation therapy or radiotherapy refers to the medical use of ionizing radiation as part of cancer treatment to control malignant cells. Radiotherapy is commonly used for the treatment of malignant tumors (cancer), and may be used as the primary therapy as well as in combination with other cancer treatments. Most common cancer types can be treated with radiotherapy in some way.

Radiation therapy decreases the size of tumors and in some cases may eradicate them. Radiation can be used to shrink tumors, allowing surgical removal that would otherwise not be possible. Because tumors and their metastases can cause pain, radiating those cancerous areas may significantly reduce pain. Radiation therapy is often used for palliation (easing symptoms from incurable cancer) and pain relief when other treatments are not possible or have not been successful.

One of the major limitations of radiotherapy is that the cells of solid tumors become deficient in oxygen. This is because solid tumors usually outgrow their blood supply, causing a low-oxygen state known as hypoxia. The more hypoxic the tumors are the more resistant they are to the effects of radiation because oxygen makes the radiation damage to DNA permanent. Much research has been devoted to overcoming this problem including the use of high pressure oxygen tanks, blood substitutes that carry increased oxygen, hypoxic cell radiosensitizers such as misonidazole and metronidazole, and hypoxic cytotoxins, such as tirapazamine.

There is still, however, a need for a method and apparatus that increase effectiveness of the radiation therapy.

SUMMARY OF THE INVENTION

In one aspect, a radiotherapy chamber is provided. The chamber comprises a substantially air-tight enclosure adapted to accept a patient; a radiation source disposed inside the enclosure; a patient support system disposed inside the enclosure and in working arrangement with the radiation source; a compressor fluidly connected to the inlet of the enclosure, and an outlet flow modulator fluidly connected to the outlet of the enclosure.

The radiation source has capacity to produce X-rays having energy in the range of about 1 to 25 MV. The radiation source may be attached to a roof, a side wall or floor of the enclosure by a support brace adapted to enable the radiation source to move in a longitudinal and circumferential direction in relation to enclosure. The patient support system comprises a patient holding section and a driving mechanism adapted to adjust position of the patient in relation to the radiation source.

In another aspect, a method of treatment of a subject in need thereof is provided. The method comprises placing the subject into a radiotherapy chamber as described above; positioning the subject in such a manner that a treatment target area is aligned with the radiation source; pressurizing the chamber to the target pressure, and treating the subject with an effective amount of radiation. During the therapy, the chamber may be maintained at the target pressure while being continuously ventilated.

DETAILED DESCRIPTION

A radiotherapy chamber is provided. Such chamber comprises a substantially air-tight enclosure adapted to accept a patient and having an inlet and an outlet; a radiation source disposed inside the enclosure; a patient support disposed inside the enclosure and in working arrangement with the radiation source; a compressor fluidly connected to the inlet of enclosure and an outlet flow modulator fluidly connected to the outlet of the enclosure.

Figure 1:
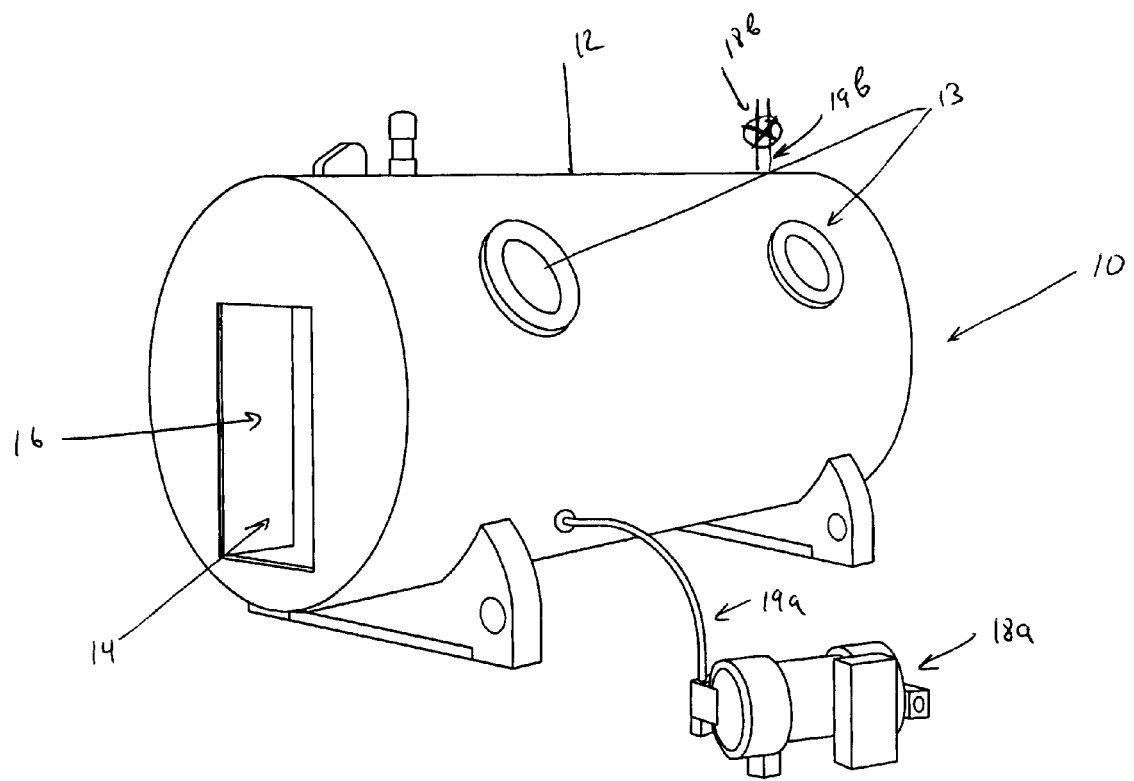
FIG. 1 is a side view of one embodiment of the radiotherapy chamber.

Referring to FIG. 1, the enclosure 12 of the radiotherapy chamber 10 is preferably a vertically-oriented, generally cylindrical structure. The enclosure 12 should be constructed in accordance with guidelines for pressure vessels set by American Society of Mechanical Engineers. Compliance with these guidelines should ensure that the enclosure 12 is capable of withstanding both hyperbaric and hypobaric environments. Preferably, the enclosure is constructed from steel or aluminum.

The enclosure 12 is adapted to enclose a patient. Additionally, the enclosure 12 should have a sufficient volume to accommodate a radiation source and a patient support system as described below. In some embodiments, the enclosure may also have room for medical personnel who can observe or assist the patients undergoing the treatment.

Referring to FIG. 1, the enclosure 12 may further comprise at least one window 13 disposed along the walls of the enclosure 12. In some embodiments the windows may also be placed on the roof of the disclosure. It is important that the windows do not allow the outside air to enter the enclosure when the enclosure is under hypobaric condition or to leak out from the enclosure when operating under hyperbaric conditions. Windows for pressure vessels are well known as illustrated by, for example, U.S. Pat. Nos. 6,639,745 or 4,986,636, incorporated herein by reference.

Access to the enclosure 12 may be gained through a sealable opening 14. Preferably, the sealable opening is designed to allow easy access to the enclosure 12. Thus, the sealable opening may be large enough to allow users to enter upright without excessive crouching. Also, preferably, it is sufficiently wide to enable medical personnel to bring patients on stretchers into the radiation chamber 10, if necessary.

The sealable opening 14 may be closed by various types of closure mechanisms 16 that have been developed over the years. Suitable closure mechanisms are described, for example, in U.S. Pat. Nos. 5,433,334; 5,327,904; 6,352,078, which are incorporated herein by reference in their entirety.

Figure 2:
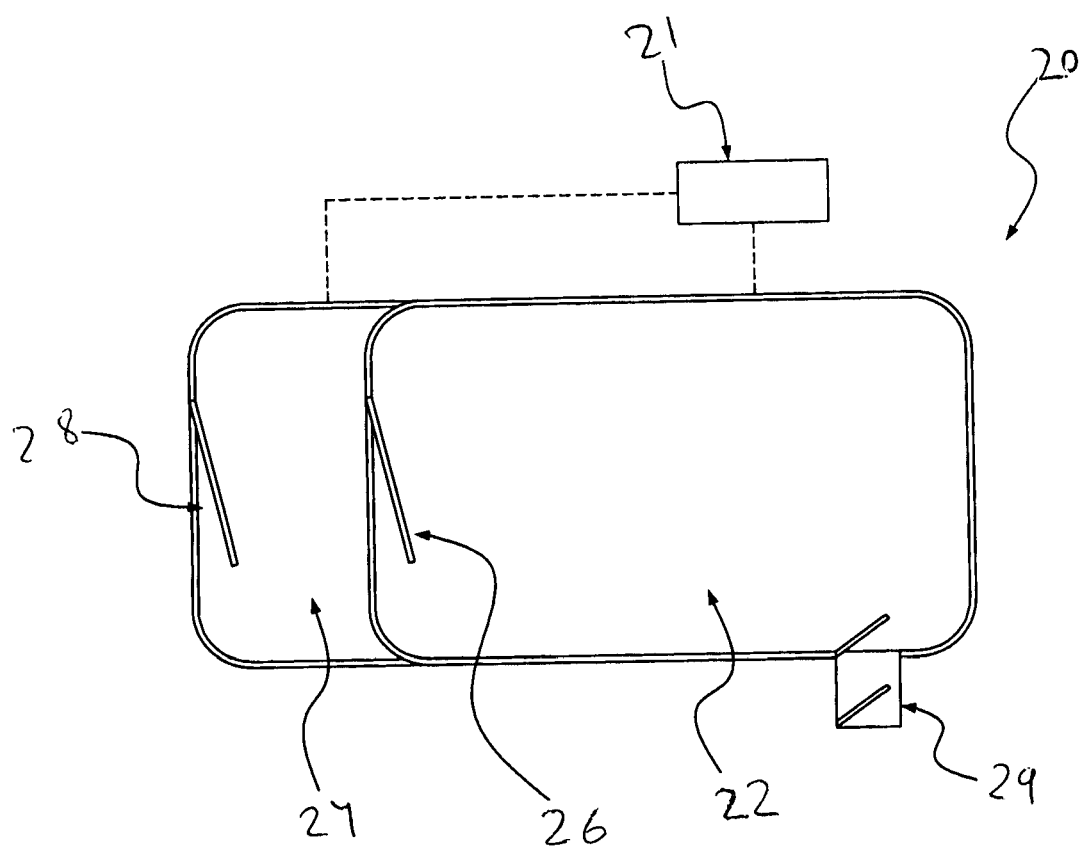
FIG. 2 shows an embodiment of the radiotherapy chamber having a dual lock entry and an air-lock.

In some embodiments, the radiotherapy chamber may include a dual lock entry. The dual lock entry allows easy access in and out of the chamber while the chamber is under pressure other than atmospheric. Referring to FIG. 2, the radiotherapy chamber 20 comprises a main enclosure 22 and an entrance enclosure 24. Once users enter the main enclosure 22, it is closed using an interior closure mechanism 26. The main enclosure may then be brought to the desired pressure using reversible compressor 21. If, for example, medical personnel need to leave while the patient is still receiving treatment, the entrance enclosure 24 is sealed by closing an exterior closure mechanism 28 and the entrance enclosure 24 is brought to the same pressure as the main enclosure 22. The interior closure mechanism 26 may then be opened so the users may move from the main enclosure 22 to the entrance enclosure 24. The interior closure mechanism 26 is then closed and the pressure in the entrance enclosure 24 is brought to the atmospheric pressure. Next, the exterior closing mechanism 28 is opened to permit the user to leave the entry enclosure 24. To allow users to enter the main enclosure 22 during treatment, the process should be reversed.

In some embodiments in addition to or instead of the dual lock entry, the radiotherapy chamber may also include an air-lock. Such airlock 29 shown in FIG. 2 allows passing of the small objects in and out of the chamber without changing the pressure in the chamber when the chamber is maintained at pressures other than atmospheric. The airlock 29 operates based on the same principal as the dual lock entry. Since the volume of the air-lock is much smaller than the volume of the entrance enclosure, it is more economical to use the air-lock to pass small objects, such as food, water, medicine, or medical instruments, in and out of the operating chamber.

To decrease the risk of fire or explosion, the chamber may preferably be pressurized with air instead of pure oxygen. In some embodiments, the users may be given individual oxygen masks that supply pure oxygen and remove the exhaled gas from the chambers. Suitable oxygen masks may simply cover the mouth and nose or they may be a type of flexible, transparent helmet with a seal around the neck. Accordingly, the chamber may also need to include a source of pure oxygen such as oxygen tank stored either inside or outside the chamber.

Preferably, the chamber also includes features that ensure the safety and comfort of the users. Such features are known and include, but are not limited, to lights, temperature control, humidity control, pressure relief valves, fire suppression systems, intercoms and combinations thereof. The chamber may also preferably include a closed-circuit camera network or similar to enable medical personnel to observe a patient inside the chamber during treatment at all times.

Figure 3:
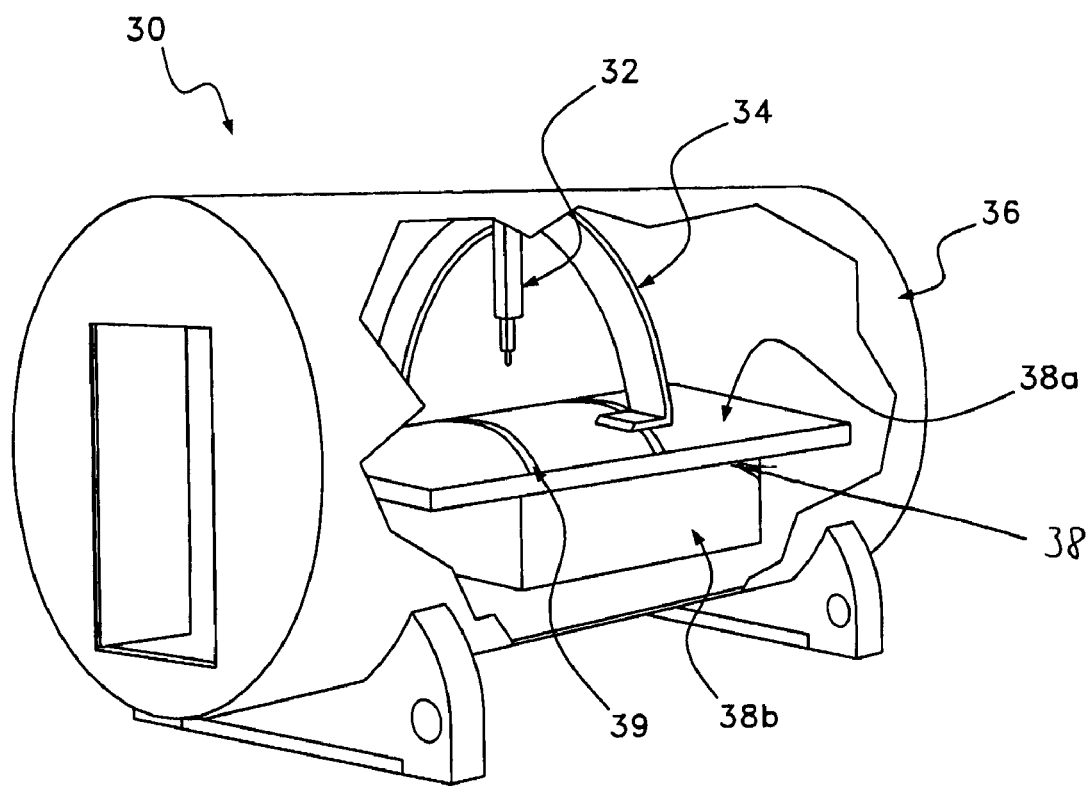
FIG. 3 shows one example of disposition of the radiation source and the patient support system inside the chamber.

Referring to FIG. 3, the radiation source 32 is disposed on the inside of the chamber 30. It may be any suitable radiation apparatus typically used in the art such as, for example, conventional external beam radiotherapy apparatus, virtual simulation radiotherapy apparatus, 3-dimensional conformal radiotherapy apparatus, and intensity-modulated radiotherapy apparatus. Suitable examples are disclosed in U.S. Pat. Nos. 6,778,850, 6,977,987 and 7,020,245, which are incorporated herein in their entirety. Preferably, the radiation source has capacity to produce X-rays having energy in the range of about 200 kilovolts to 25 megavolts, and more preferably in the range of 1 to 25 megavolts. It may be attached to the roof, side wall or the floor of the chamber using a support brace 34. The support brace 34 can be of any type that enables the radiation source 32 to be moved in longitudinal direction or in circumferential direction in relation to enclosure 36, or be pivoted. Alternatively, the radiation source may be a part of the free-standing radiation apparatus.

The radiation chamber 30 also includes a patient support system 38 disposed on the inside of the chamber. The patient support system 38 is in working arrangement with the radiation source 32 which means that their positions can be adjusted in relation to each other to enable alignment of the treatment target area of the patient with the radiation source, as described below. The patient support system 38 comprises a patient holding section 38a and a driving mechanism 38b. The driving mechanism 38a is adapted to move the patient holding section 38b in longitudinal and the lateral direction of the enclosure 36, or up and down. The driving mechanism 38b may also pivot the patient holding section. Suitable examples of patient support systems are disclosed in U.S. Pat. Nos. 6,094,760 and 7,011,447, incorporated herein in their entirety. In some embodiments, the radiation source and the patient support system may be connected by a support brace or similar such as, for example, disclosed in U.S. Pat. No. 6,888,919, incorporated herein by reference in its entirety. The patient support system 38 may also include devices 39 to secure the patient to the patient holding section.

Referring back to FIG. 1, the radiation chamber 10 also includes a reversible compressor 18a fluidly connected to the enclosure 12 via a hose or a pipe 19a and an air flow modulator 18b connected to the enclosure by a hose or a pipe 19b. Suitable compressors have capability to pressurize the enclosure to pressure between 1 and 6 atmospheres or to depressurize the enclosure to about 0.1 atmospheres, as desired for specific applications. Preferably, a high speed modulator valve is used such that it can fully open and close in less than one second. Flow modulators are well known in the art and are described, for example in, *Control Valve Handbook*, 4th *edition*, Fisher Controls International, (2005), incorporated herein by reference in its entirety. One suitable example of an outlet modulator valve is an electro-pneumatic positioner manufactured by Radius, LLS, Milford, Mich. (part # RX-1000 series; R-AD-012). A person with ordinary skill in the art is undoubtedly capable of selecting a compressor and an outlet flow modulator that in combination may enable the target pressure to be achieved and maintained in the chamber, while allowing the chamber to be continuously ventilated with a fresh air supply.

In a typical multi-person hyperbaric chamber, a medical grade compressor supplies the primary air at pressure of up to 125 psi. This air then passes through a sequence of conditioning equipment such as an after cooler, a oil separator, an air dryer and some sort of filtration package, before it is held at high-pressure in a sequence of air reservoirs. In order to maintain proper operations, the air reservoirs typically have the capacity of holding at least two times of the air volume that the chamber needs.

From the reservoirs, the pressurized air is passed through another air dryer to remove condensation potentially collected during the cooling process of the air while setting latent in the reservoirs, is passed through a water separator to remove the condensation created by the air dryer, and is passed through some sort of a particulate filtration system. In the last step, the air pressure is regulated down to the operating pressure required by the chamber using a regulator flow valve. Once the chamber is pressurized, no additional, "fresh", air is supplied to the chamber. Accordingly, to maintain the air quality within medical guidelines and to keep the patient somewhat comfortable, the internal air of the chamber has to be scrubbed for carbon dioxide and circulated through some form of internal air-conditioning unit.

In addition to requiring multiple stages of equipment and numerous reduction, control, and relief valves to transfer the compressed air from the holding reservoirs into the chamber, the above-described process also causes great discomfort to the patients. While the chamber is being brought up to its operating pressure, adiabatic heat is produced by the recompression of the air inside the chamber. Conversely, during depressurizing of the chamber, the air is rapidly chilled. These drastic changes in temperature are extremely uncomfortable for the occupants of the chamber.

In the preferred embodiment, the reversible compressor comprises a screw compressor. Screw compressors are typically used to transfer dry bulk materials such as cement, flour, salt, and milk powder, and to convey, boost or compress a myriad of inert, corrosive, and explosive gases found in chemical plants and refineries. Applicants, however, unexpectedly found that using screw compressors for pressure chambers results in a number of benefits. These benefits include, but are not limited to: enabling chamber operation under both hypobaric and hyperbaric conditions without need for additional equipment; enabling user to pressurize and use the air for the chamber in one continuous action instead of pressurizing the air to high PSI, storing it, and using multiple stages of conditioning equipment to make it suitable for human use; reducing a quantity of required equipment; eliminating patient discomfort; allowing fresh air circulation.

Generally, a screw compressor may supply a constant high volume of air that maintains its flow curve against any restriction until it reaches its design high pressure limit. In one embodiment, by supplying the chamber's ambient air at a constant flow rate and restricting its exhaust capacity flowing through the chamber by use of a high-speed modulating valve, the end result is an extremely controllable and sustainable rate of pressurization. Alternatively, the exhaust capacity may be maintained at a constant value, and the chamber may be pressurized by varying the flow rate of air from the screw compressor. Once the target pressure value has been achieved, it can be by use of programmable industrial automation controls.

Preferably, by screw compressor supplying a constant flow (CFM) of air during the entire pressure curve of the treatment, the system computers may be capable of continuously controlling the target pressure to plus or minus 0.01 PSI, while continuously ventilating the chamber with a fresh air supply. In other words, when the system reaches a pressurized steady state, it may be maintained by adjusting the compressor and the outlet flow modulator so the amount, mass, of fresh air flowing into the chamber is equal to the amount of air flowing out from the chamber and exhausted out of the system. The term "fresh air" means the air supplied by the compressor that has not been previously used to pressurize the chamber.

Accordingly, in one embodiment the pressure in the chamber is maintained by continuously pumping air into the chamber; continuously exhausting the air from the chamber to atmosphere; and continuously monitoring the pressure in the chamber and adjusting the input or output to maintain pressure in the chamber.

Screw compressors supply dry, oil free air at temperatures of up to 340° F. sterilizing the air, which may then be chilled through the use of a flow controlled chilled water source, supplying a high-efficiency heat exchanger that lowers the adiabatic heat of compression to a comfortable 55 to 85° F. Any condensation created from the process may be easily collected and removed. Mist filtration preferably removes 99.9% of any particular matter 1/10 of a micron or larger. By preconditioning the air temperature before it ever reaches the hyperbaric chamber, the occupants never feel an uncomfortable rise or fall of the temperature inside the chamber.

Any known screw compressor may be employed. One suitable example includes, but is not limited to, Aerzen Screw Compressor units DELTA SCREW VM/VML manufactured and sold by Aerzen USA, Coatesville, Pa. These compressors are specifically designed for dry and clean compression of air and neutral gases. They may be used for oil-free compression of air and inert gases up to 8500 cfm (14,400 m$^3$/h) and 30 psig or 5600 cfm (9500 m$^3$/h) up to 51 psig. These machines may also be used as very efficient dry screw vacuum pumps down to 85% continuous vacuum or 25.5"Hg.

Figure 4A:
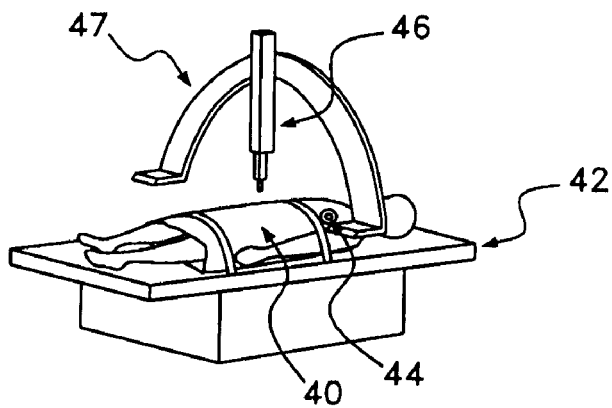
FIG. 4 show illustrates positioning the subject to align a treatment target area with the radiation source.
Figure 4B:
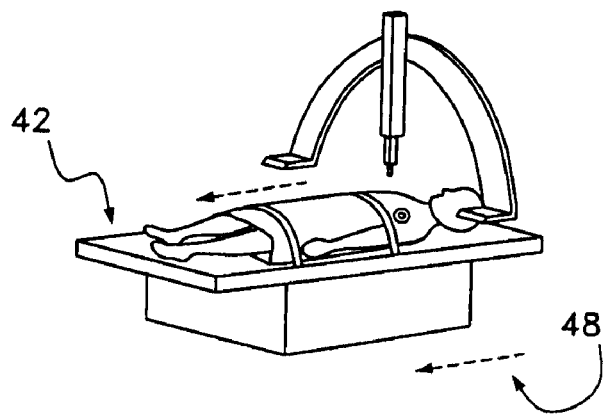
Figure 4C:
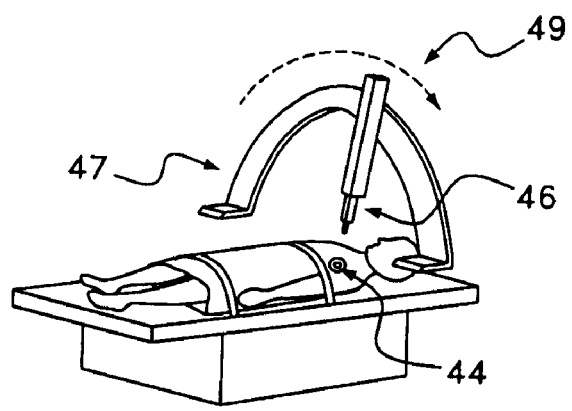

In another aspect, a method of treatment of a subject in need thereof is provided. Referring to FIG. 4a, the subject 40 is first placed on the patient support system 42 inside the radiotherapy chamber as described above. The subject 40 is then positioned in such a manner that a treatment target area 44 is aligned with the radiation source 46 as shown in FIG. 4b. This can be achieved by moving the patient holding section, the radiation source or both. For example, in FIG. 4b, the patient support system 42 is first moved in longitudinal direction as indicated by arrow 48 in FIG. 4b. The radiation source is then moved in circumferential direction along the support brace 47 as indicated by arrow 49 in FIG. 4c. As a result, the treatment target area 44 is aligned with the radiation source 46 as illustrated in FIG. 4c.

Then, the pressure in the pressure chamber may be increased in accordance with desired effect on the subject. Such pressure will be referred to herein as target pressure. The pressure in the variable chamber may be increased to up to 6 atmospheres, preferably between about 1.5 and 3 atmospheres, and more preferably between about 2.0 to 2.4 atmospheres. Finally, the subject may be exposed to an effective amount of radiation. An effective amount means an amount of radiation which, when administered to a subject, is sufficient to result in an improvement in patient's condition. The improvement maybe determined in a variety of ways. Additionally, the improvement does not mean a cure and may include only a marginal change in patient's condition.

A person with the ordinary skill in the art will undoubtedly be able to determine the effective amount for different conditions. The effective amount varies depending on the type and stage of cancer being treated. For curative (radical) cases, the typical dose for a solid epithelial tumor ranges from 50 to 70 Grays ("Gy"), while lymphoma tumors are treated with 20 to 40 Gy. Preventative (adjuvant) doses are typically around 50-60 Gy in 2 Gy fractions (for Breast, Head and Neck cancers respectively.) Many other factors may be considered when selecting a dose, including whether the patient is receiving chemotherapy, whether radiation therapy is being administered before or after surgery, and the degree of success of surgery. The dosage may be fractioned. For example, the typical fractionation schedule for adults is 1.8 to 2 Gy per day, five days a week. By placing a patient in a hyperbaric environment, you can use less chemotherapy and or radiation with increased effect.

Figure 5:
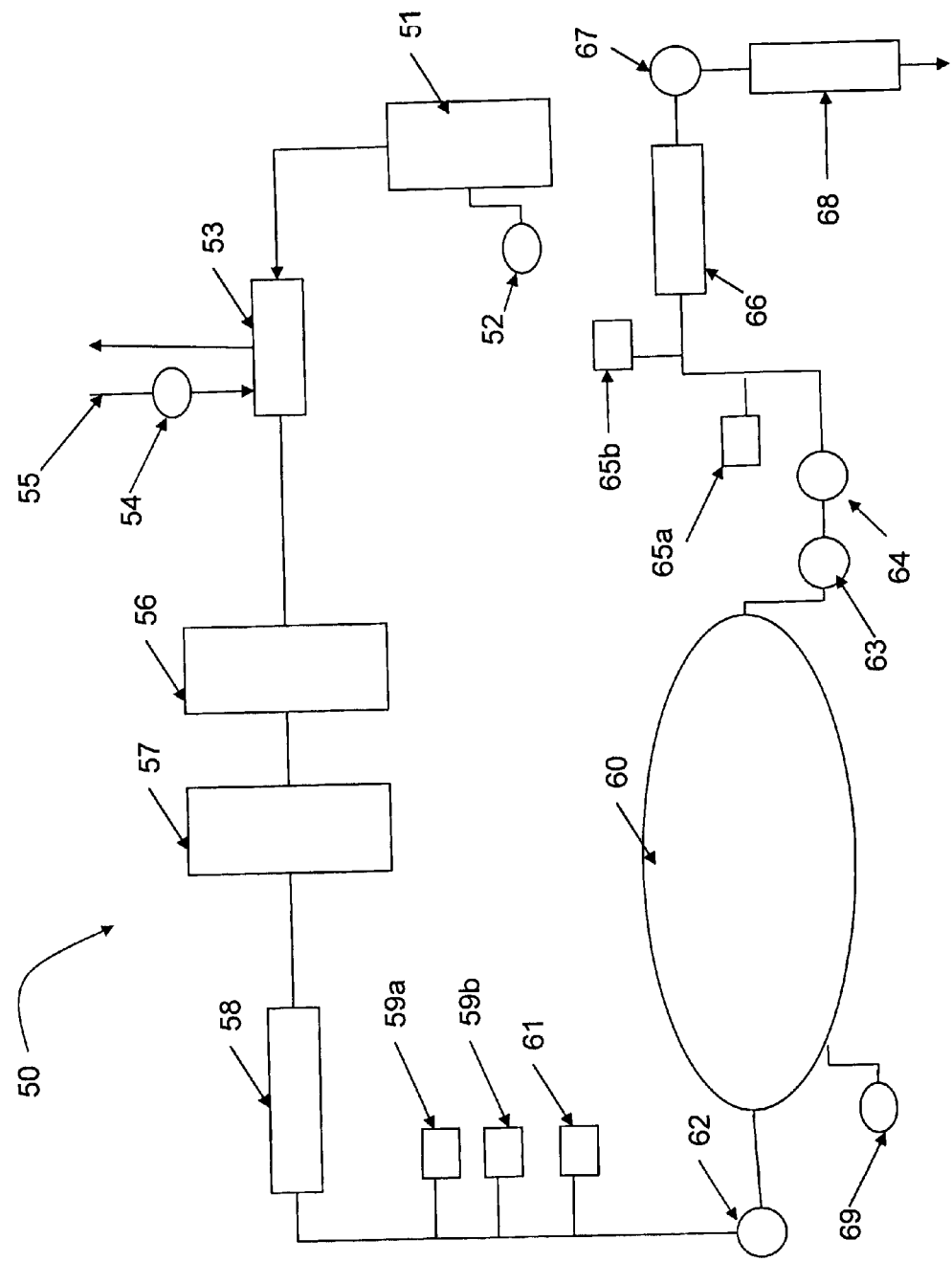
FIG. 5 presents an embodiment flow chart.

FIG. 5 presents a non-limiting embodiment process flow chart for a variable pressure chamber with a screw compressor system 50. The oil free air may exit the compressor 51, which may include a release valve 52, at approximately 340° F. and 30 psi. The high temperature sterilizes the air immediately destroying any biological or microbial life. The air may then be passed through a non-restrictive heat exchanger 53 that drops the air temperature to about 65° F. Conversely, during the depressurization cycle of the process, air supply may be preheated to maintain the internal temperature of the chamber at a comfortable 70 to 72° F. The temperature of the air may be controlled by a modulating valve 54 which controls the flow rate of chilled water supply 55. Controlling the temperature in this manner is possible because the air is only compressed one time in the chamber and then is maintained at that pressure through control of the constant flow. On the contrary, in a typical chamber, the temperature of the air in the chamber cannot be controlled because the air is recompressed inside the chamber.

The air supply is then passed through a pre-filter 56 to remove any condensation formed by the rapid chilling process and then through a mist eliminator 57 to remove submicronic particles and to reduce residual moisture content. For this application, it is desirable to use a mist eliminator capable of removing particles at a rate of 99.98% of particles $\frac{1}{10}$ micron and larger and of reduces any residual moisture content down to 0.5 ppm. Optionally, the airflow may be passed through an acoustic attenuator, silencer, 58 that may reduce any sound generated in the compression or filtration process to less than 70 dB. The air is then passed through a series of primary controls 59, described below, and into the chamber 60 through a pressure gauge 61 and a check valve 62. After the chamber, the air is passed through air velocity fuse 63, isolation valve 64, a series of secondary controls 65, a silencer 66, an outlet flow modulator valve 67, and another silencer 68 before it is exhausted from the system. The pressure in the chamber may be achieved and controlled by a modulator valve 67. Preferably, a high speed modulator valve is used so it can fully open and close in less than one second. The chamber may also include an emergency relief valve 69.

The flow rate and physical characteristics of air may be controlled by two sets of controller 59 and 65. A primary set of controllers 59 comprises a temperature sensor 59a and pressure sensor 59b. The secondary set of controllers 65 comprises temperature sensor 65a and pressure sensors 65b. In addition, the exhaust air may also be sampled using an air quality system 51 for oxygen percentage and carbon dioxide. These data is supplied to the controller unit (not shown) that may adjust the air flow rate to achieve desired pressure, temperature, etc. Any type of controllers may be used for the methods described herein. Preferably, a feedback controller, such as for example a proportional-integral (PI) or a proportional-integral-derivative controller (PID controller), is utilized. Preferably, continual updates from the processor are taken at a speed of 5 ms which enables precise control of the airstream.

All publications cited in the specification, both patent publications and non-patent publications are indicative of the level of skill of those skilled in the art to which this invention pertains. All of these publications are herein fully incorporated by reference to the same extent as if each individual publication were specifically and individually indicated as being incorporated by reference.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the following claims.

What is claimed is:

1. A radiotherapy chamber comprising:
    a substantially air-tight enclosure adapted to accept a patient and having an inlet and an outlet;
    a radiation source disposed inside the enclosure and attached to a roof, a side wall, or a floor of the enclosure by a support brace adapted to enable the radiation source to move in longitudinal and circumferential direction in relation to enclosure;
    a patient support system disposed inside the enclosure and in working arrangement with the radiation source;
    a screw compressor fluidly connected to inlet of the enclosure, and
    an outlet flow modulator fluidly connected to the outlet of the enclosure,
    wherein the screw compressor supplies a constant flow rate of air into the enclosure to maintain, in combination with the outlet flow modulator, constant target pressure in the enclosure while continuously ventilating the chamber with a fresh air supply.

2. The radiotherapy chamber of claim 1, wherein the air tight enclosure has capacity to withstand hyperbaric pressure.

3. The radiotherapy chamber of claim 1, wherein the radiation source is an X-ray source.

4. The radiotherapy chamber of claim 1, wherein the radiation source has capacity to produce x-rays having energy in the range of about 1 to 25 MV.

5. The radiotherapy chamber of claim 1, wherein the radiation source is a free standing apparatus.

6. The radiotherapy chamber of claim 1, wherein the patient support system comprises a patient holding section and a driving mechanism adapted to adjust position of the patient in relation to the radiation source.

7. The radiotherapy chamber of claim 1 further comprising:
    a sealable opening adapted to provide access to the enclosure;
    a closure mechanism adapted to seal the sealable opening.

8. The radiotherapy chamber of claim 1 wherein the compressor is a reversible compressor.

9. The radiotherapy chamber of claim 1, wherein the target pressure is maintained to plus or minus 0.01 PSI.

10. A method of treatment of a subject in need thereof comprising:
    placing the subject into a radiotherapy chamber comprising:
        a substantially air-tight enclosure adapted to accept a patient and having an inlet and an outlet;
        a radiation source disposed inside the enclosure and attached to a roof, a side wall, or a floor of the enclosure by a support brace adapted to enable the radiation source to move in longitudinal and circumferential direction in relation to enclosure;
        a patient support system disposed inside the enclosure and in working arrangement with the radiation source; and
        a screw compressor fluidly connected to inlet of the enclosure; and
        an outlet flow modulator fluidly connected to the outlet of the enclosure,
    pressurizing the chamber to a target pressure;
    positioning the subject in such a manner that a treatment target area is aligned with the radiation source;
    treating the subject with an effective amount of radiation, and
    running the compressor to supply a constant flow rate of air into the enclosure throughout the treatment; and using the compressor and the outlet flow modulator in combination to maintain constant target pressure in the enclosure while continuously ventilating the chamber with a fresh air supply.

11. The method of claim 10, wherein the radiation source has capacity to produce x-rays having energy in the range of about 1 to 25 MV.

12. The method of claim 10, wherein the patient support system comprises a patient holding section and a driving mechanism adapted to adjust position of the patient in relation to the radiation source.

13. The method of claim 10, wherein the target pressure is maintained to plus or minus 0.01 PSI.

14. A radiotherapy chamber comprising:
a substantially air-tight enclosure adapted to accept a patient and having an inlet and an outlet;
a radiation source disposed inside the enclosure and attached to a roof, a side wall or a floor of the enclosure by a support brace adapted to enable the radiation source to be moved in longitudinal and circumferential direction in relation to enclosure;
a patient support system disposed inside the enclosure and in working arrangement with the radiation source; and
a compressor fluidly connected to inlet of the enclosure.

* * * * *